(12) United States Patent
Persson

(10) Patent No.: US 6,921,417 B2
(45) Date of Patent: Jul. 26, 2005

(54) TRACHEOSTOMA VALVE

(75) Inventor: Jan-Ove Persson, Höör (SE)

(73) Assignee: Atos Medical AB, Hörby (SE)

( * ) Notice: Subject to any disclaimer, the term of this patent is extended or adjusted under 35 U.S.C. 154(b) by 178 days.

(21) Appl. No.: 09/994,706

(22) Filed: Nov. 28, 2001

(65) Prior Publication Data

US 2002/0156527 A1 Oct. 24, 2002

(51) Int. Cl.$^7$ .................................................. A61F 2/20
(52) U.S. Cl. ............................................................ 623/9
(58) Field of Search ...................... 623/9, 2.1, 3.1–3.25, 623/10

(56) References Cited

U.S. PATENT DOCUMENTS

| | | | | |
|---|---|---|---|---|
| 2,804,076 A | * | 8/1957 | Giraudon | 128/207.16 |
| 3,137,299 A | * | 6/1964 | Tabor | 128/207.16 |
| 4,040,428 A | * | 8/1977 | Clifford | 128/207.16 |
| 4,325,366 A | * | 4/1982 | Tabor | 128/207.16 |
| 4,582,058 A | * | 4/1986 | Depel et al. | 128/207.17 |
| 4,596,248 A | * | 6/1986 | Lieberman | 128/207.16 |
| 4,759,356 A | * | 7/1988 | Muir | 128/207.16 |
| 4,911,716 A | * | 3/1990 | Blom et al. | 623/9 |
| 4,971,054 A | * | 11/1990 | Andersson et al. | 128/207.16 |
| 5,059,208 A | * | 10/1991 | Coe et al. | 623/9 |
| 5,259,378 A | * | 11/1993 | Huchon et al. | 128/207.16 |
| 5,391,205 A | * | 2/1995 | Knight | 623/9 |
| 5,392,775 A | * | 2/1995 | Adkins et al. | 128/207.16 |
| 5,487,382 A | * | 1/1996 | Bezicot | 128/207.14 |
| 5,738,095 A | * | 4/1998 | Persson | 128/207.14 |
| 5,806,515 A | * | 9/1998 | Bare et al. | 128/207.15 |
| 6,422,235 B1 | * | 7/2002 | Persson | 128/200.26 |
| 2004/0089291 A1 | * | 5/2004 | Persson | 128/200.16 |

FOREIGN PATENT DOCUMENTS

| | | |
|---|---|---|
| DE | 3436777 A1 | 4/1985 |
| EP | 0078685 A1 | 11/1983 |
| WO | WO 9517138 A1 | 6/1995 |

* cited by examiner

Primary Examiner—Alvin Stewart

(57) ABSTRACT

A vocal valve to be applied to a tracheostomized person's neck comprises an air passage to be connected with the tracheostoma for connecting the trachea with the surroundings. A check valve member is provided in the air passage, wherein the check valve member is normally closed but allows for inhalation through the air passage. The vocal valve further comprises a manually adjustable member for establishing a free air flow through the air passage at inhalation as well as exhalation.

9 Claims, 2 Drawing Sheets

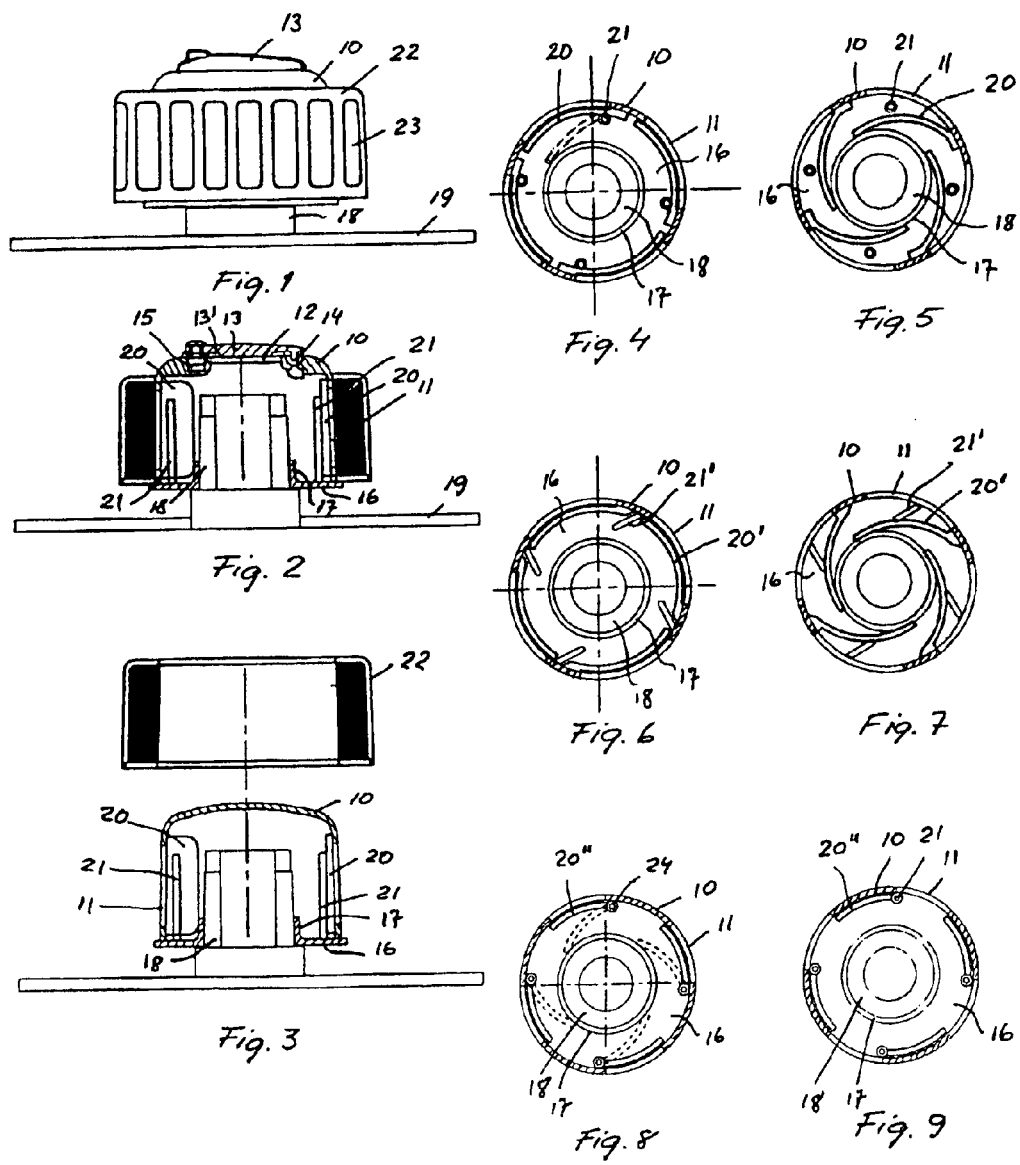

TRACHEOSTOMA VALVE

Figure 10:
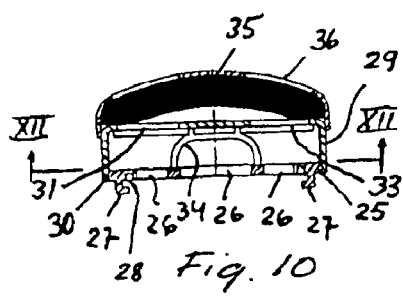

The invention relates to a vocal valve to be applied to the neck of a tracheostomized but not laryngectomized person, i.e. a person who has still the larynx with epiglottis and vocal cords and therefore can use the upper air passages and also can speak in the normal manner under certain conditions. However, this does not apply to an laryngectomized person who breathes continuously through a tracheostoma and in order to produce speech must have a fistula in the wall between trachea and esophagus with a voice prosthesis inserted therein speech being produced by closing the tracheostoma and forcing air from trachea via the voice prosthesis into esophagus the walls of which are brought to vibrate under production of speech. The reason for a non-laryngectomized person being tracheostomized may be that breathing shall be facilitated or direct communication with trachea is required for treatment in a respirator after a severe accident. Other reasons may be the appearance of asthmatic attacks, pulmonary decease or apnea under sleeping of very fat persons.

According to generally applied terminology a tracheostomized person is a person who has a tracheostoma and has still the larynx (with epiglottis and vocal cords) while a laryngectomized person is a person who has a tracheostoma but whose larynx has been removed by surgery. This terminology henceforth will be used herein.

A tracheostomized person cannot speak when the tracheostoma is open because the exhalation air partly disappears through the tracheostoma and too little air passes the vocal cords in order that speech shall be produced. In order that such a person shall be able to speak the tracheostoma thus must be closed, and for this purpose a vocal valve is used, which controls the connection between trachea and the surroundings via the tracheostoma.

The person thus inhales through the tracheostoma and exhales through the normal upper breathing passages and speaks in a normal manner. This differentiates the vocal valve for a tracheostomized person from such vocal valves which are used by laryngectomized persons. These latter valves are normally open so that inhalation as well as exhalation can take place through the vocal valve, which is necessary because the tracheostoma is the sole connection between trachea and the surroundings. When speech shall be produced via the voice prosthesis inserted in the fistula the exhalation air flow is suddenly increased in order that the vocal valve shall close at a certain air flow rate and the exhalation air shall be expelled via the voice prosthesis.

In some cases a tracheostomized person due to difficulties to exhale through the upper air passages, e.g. due to temporary or chronic illness, may be embarrassed by the exhalation through the upper air passages requiring some effort. Therefore, the person may desire to relieve himself or herself from this effort under periods when exhalation through the upper air passages is not necessary for the production of speech, by inhaling as well as exhaling through the tracheostoma during these periods.

The vocal valve according to the invention is intended for tracheostomized persons and is of the kind comprising an air passage to be connected to the stoma in order to connect trachea with the surroundings, and a check valve member in the air passage, normally closed but allowing inhalation through said passage, and the object of the invention is to create in a vocal valve of this kind conditions for inhalation and exhalation through the tracheostoma in a manner that is comfortable for the user, without apparatus change and without adverse influence on the possibility to produce speech in the normal manner by means of the vocal cords when desired.

Said object is achieved by the vocal valve having been given the characterizing features of claim 1.

In order to avoid problems with the function of the lungs and trachea the inhalation air should be heated and moistened which in healthy persons takes place in the nose. A laryngectomized person always inhales as well as exhales through the tracheostoma and the vocal valve connected therewith, and in this case the vocal valve can be combined with a heat and moisture exchanger often called HME, which takes up heat and moisture from the exhalation air and returns heat and moisture to the inhalation air.

According to a further development the vocal valve according to the invention therefore is combined with a heat and moisture exchanger through which the inhalation air as well as the exhalation air is allowed to pass when the vocal valve is set for free air flow through the air passage so that an effective heat and moisture exchange then is achieved.

Figure 11:
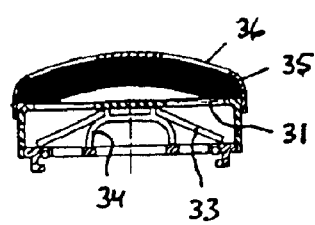
Figure 14:
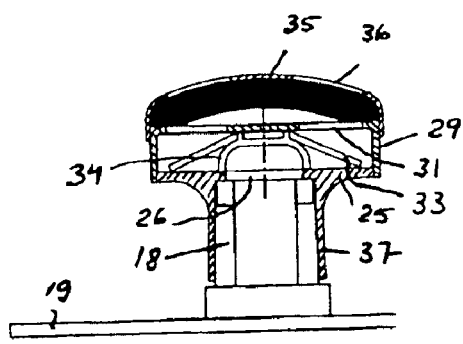
Figure 12:
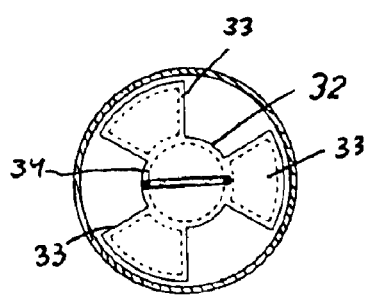
Figure 13:
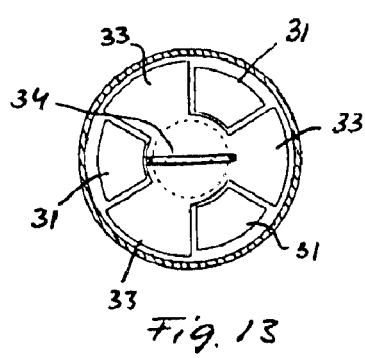

In order to explain the invention in more detail illustrative embodiments of the vocal valve according to the invention will be described below reference being made to the accompanying drawings in which FIG. 1 is a side view of a vocal valve according to the invention with cough function, FIG. 2 is an axial cross-sectional view of the vocal valve in FIG. 1, FIG. 3 is an axial cross-sectional view of a vocal valve according to the invention without cough function the heat and moisture exchanging element being shown separated from the rest of the vocal valve, FIG. 4 is a cross-sectional view of the vocal valve and shows the valve in speech position, FIG. 5 is a corresponding view as that in FIG. 4 of the vocal valve in heat and moisture exchanging position, hereinafter referred to as HME position, FIGS. 6 and 7 are views similar to FIGS. 4 and 5 of another embodiment of the vocal valve, FIGS. 8 and 9 are views similar to FIGS. 4 and 5 of a third embodiment of the vocal valve, FIG. 10 is an axial cross-sectional view of a fourth embodiment of the vocal valve shown in exhalation position, FIG. 11 is a corresponding view of the vocal valve in FIG. 10 shown in inhalation position, FIG. 12 is a cross-sectional view along line XII—XII in FIG. 10 of the vocal valve in FIGS. 10 and 11 without HME element and with the vocal valve shown in speech position, FIG. 13 is a corresponding view as FIG. 12 with the vocal valve in HME position, and FIG. 14 is an axial cross-sectional view of the vocal valve according to FIGS. 10–13 but with a modified attachment device the vocal valve being shown in inhalation position.

Referring to FIGS. 1, 2, 4 and 5 the embodiment of the vocal valve according to the invention disclosed therein comprises a housing 10 open at the bottom and having circular cross-section. In the circular wall side openings 11 are provided, and in an end wall closing the housing at the top thereof a central opening 12 is provided. A valve flap 13 with a seal 13' is hinged to the housing at 14 and is maintained in a position closing the opening 12 by means of two magnets 15 one of said magnets being provided on the housing and the other one on the valve flap. The housing 10 is mounted for rotation on a bottom plate 16 closing the lower open end of the housing and forming a hollow stud 17 by means of which the plate and thus the vocal valve is detachably mounted to an ISO cone 18 having wings 19 which can be attached to a flexible collar of plastic which is taped to the patient's neck over a tracheostoma with the ISO cone communicating with trachea. It is most common, however, that the ISO cone forms part of a straight or curved tracheal cannula which is passed through the tracheostoma into trachea and forms a stent in the tracheostoma the wings 19 being integral with the tracheal cannula and engaging the neck of the patient. The tracheal cannula preferably is formed with fenestration, i.e. side apertures in the portion thereof to be located inside trachea.

On the inside surface of the circular wall of the housing 10 flexible membranes 20 of rubber or the like are provided one for each side opening 11, said membranes being dimensioned to cover each one side opening but being curved according to FIG. 5 in the relieved position thereof so that the associated side opening is uncovered. On the bottom plate there is provided for each membrane an axially extending cylindrical pin 21 which in one rotated position of the housing 10, FIG. 4, engages the membrane and maintains the membrane in such a position that it covers the associated side opening 11 the membrane matching the shape of the inside surface of the circular wall of the housing. In another rotated position of the housing (FIG. 5) wherein the housing is rotated clockwise a quarter of a revolution from the position in FIG. 4, the pin is disengaged from the associated membrane so that the membrane can take the relieved position according to FIG. 5 with the side opening uncovered. In this position of the pins 21 the membranes 20 are prevented from closing the openings 11 at exhalation.

A HME cassette 22 i.e. a cassette which contains a heat and moisture exchanging material which is uncovered in side apertures 23 on the outside of the cassette and is completely uncovered on the inside of the cassette is for one way use and is passed onto the housing 10. It can easily be removed therefrom for replacement when required. In FIG. 3 the HME cassette is shown separated from the housing 10 which in this figure is shown without cough function, which means that the valve flap 13 is omitted and that the end wall of the housing 10 is unperforated.

Normally the vocal valve takes the position shown in FIG. 4 which can be defined as the speech position. The membrane 20 prevents exhalation through the tracheostoma and the vocal valve so that the exhalation air instead escapes via the upper air passages and the vocal cords for the production of speech. In order that the flow resistance for the exhalation air shall not be too great it is important that the tracheal cannula is fenestrated so that the exhalation air easily can pass through the cannula. At inhalation the membranes are sucked in uncovering of the associated openings in the circular wall of the housing as indicated by dotted lines regarding one of the membranes in FIG. 4.

The patient can rotate the housing to the position according to FIG. 5 in order that the housing shall be set in this position under periods when it is not necessary to produce speech and inhalation as well as exhalation via the tracheostoma then can take place unobstructedly through the vocal valve and the HME cassette mounted thereon under supply of heat and moisture to the HME cassette from the exhalation air while the inhalation air takes up heat and moisture from the HME cassette.

The valve flap 13 forms a cough valve which normally is held in a closed position by means of the magnets 15. At a cough attack the overpressure arising in the vocal valve overcomes the adhesion force of the magnets so that the valve flap will be brought to an open position.

In the embodiment according to FIGS. 6 and 7 the membranes 20' are constructed in such a way that they take the speech position according to FIG. 6 in the relieved condition thereof. The pins 21' in this case are plate-shaped in order to cam the membranes to the open position according to FIG. 7 when the housing is rotated a quarter of a revolution clockwise from the position according to FIG. 6 in order to take the HME position according to FIG. 7. The edge of the pins which is engaged with the membrane then preferably is gently rounded. The function in other aspects is the same in this embodiment as described above.

The embodiment in FIGS. 8 and 9 comprises membranes 20" which are attached to axially extending pins 24 and are curved in accordance with the inside surface of the circular wall of the housing 10. In the speech position according to FIG. 8 the membranes cover the side openings 11 and then prevent exhalation but can be brought to the open position indicated by dotted lines by inhalation. By rotation of the housing clockwise to the position according to FIG. 9 the side openings will be completely uncovered and unobstructed inhalation and exhalation can take place via the HME cassette and the side openings.

The embodiments in FIGS. 10–14 are axial embodiments but function principally in the same way as the embodiments described above.

In the embodiment according to FIGS. 10–13 a circular bottom plate 25 is provided having openings 26 and members 27 for attachment of the bottom plate to some form of adapter which is attached over the tracheostoma, instead of attachment to an ISO cone. In the lower side of the bottom plate an annular groove is provided with a sealing ring 28 for sealing between the bottom plate and the adapter. A housing 29 open at the bottom thereof and having circular cross-section is rotatably mounted to the bottom plate by the peripheral edge thereof being received by an inside annular groove 30 in the inside of the circular wall of the housing. In the end wall of the housing three flow openings 31 are provided which can be closed by means of a check valve element 32 forming three flaps 33 each sufficiently large to cover one of the openings 31. The check valve element 32 is supported by a standard 34 formed by the plate. The openings 31 are covered by a HME cassette 35 which is of one way type and is detachably mounted to the housing 29. The HME cassette contains a heat and moisture exchanging material which is completely uncovered towards the openings 31 in the housing 29 and towards the surroundings through openings 36 in the cassette.

The vocal valve is in the speech position when the housing is set according to FIG. 12. In this position the flaps 33 are located in register with their associated openings 31 so that at exhalation they are pressed against the end wall of the housing and cover said openings, FIG. 10, and at inhalation uncover the openings 31 by the flaps 33 then taking the position shown in FIG. 11. Now, if the housing 29 is rotated to the position according to FIG. 13 in which the openings 31 are located in the notches between the flaps 33 a free passage will be established between the tracheostoma and the surroundings via the filter cassette 35 at inhalation as well as exhalation.

The embodiment according to FIG. 14 functions in the same manner as just described. The constructive difference between this embodiment and the embodiment according to FIGS. 10–13 is that the bottom plate 25 at the lower side thereof forms a tubular socket 37 which is dimensioned to fit on an ISO cone 18.

What is claimed is:

1. A vocal valve to be mounted to a tracheostomized person's neck, comprising:

an air passage to be connected to the tracheostoma for connecting trachea with atmospheric surroundings;

a heat and moisture exchanging element provided in the air passage;

a check valve member in the air passage normally closed but allowing inhalation through the air passage; and a manually adjustable member for establishing a free air flow through the air passage at inhalation as well as exhalation, said manually adjustable member comprising a housing rotatably mounted to a bottom plate for connection to the tracheostoma and enclosing the check valve member.

2. The vocal valve according to claim 1, wherein the interior of the housing through at least one opening in the wall of the housing communicates with the atmospheric surroundings via the heat and moisture exchanging element.

3. The vocal valve according to claim 2, wherein the heat and moisture exchanging element is detachably mounted to the housing on the outside surface thereof.

4. The vocal valve according to claim 2, wherein the check valve member is constructed to cover in the closed position thereof the opening and to block the air passage there through.

5. The vocal valve according to claim 4, wherein the check valve member comprises an elastic membrane which is constructed to keep the opening uncovered in a relieved condition thereof.

6. The vocal valve according to claim 5, further comprising:

a member which is displaceable by rotating the housing in relation to the elastic membrane is constructed to keep the elastic membrane in a position covering the opening in one rotated position of the housing, and to allow the relieved condition of the elastic membrane with the opening uncovered in another rotated position of the housing.

7. The vocal valve according to claim 4, wherein the check valve member comprises an elastic membrane which is constructed to take a position in a relieved condition thereof wherein the opening is covered.

8. The vocal valve according to claim 7, further comprising:

a member displaceable by rotation of the housing in relation to the elastic membrane is constructed to keep the elastic membrane in a position in which the opening is uncovered, in one rotated position of the housing.

9. The vocal valve according to claim 8, wherein the displaceable member is mounted stationarily on the bottom plate and the elastic membrane is located on the inside of the wall of the housing to be rotatable together with the housing.

* * * * *